US00PP09642P

United States Patent [19]

Dehan

[11] Patent Number: Plant 9,642

[45] Date of Patent: Sep. 10, 1996

[54] ASTER PLANT NAMED 'SUNBIRD'

[75] Inventor: Klara Dehan, Holon, Israel

[73] Assignee: Danziger "Dan" Flower Farm, Moshav Mishmar Hashiva, Israel

[21] Appl. No.: 471,562

[22] Filed: Jun. 6, 1995

[51] Int. Cl.[6] ..... A01H 5/00

[52] U.S. Cl. ..... Plt./68.1

[58] Field of Search ..... Plt./68.1

*Primary Examiner*—James R. Feyrer

*Attorney, Agent, or Firm*—Foley & Lardner

[57] ABSTRACT

A new and distinct cultivar of Aster plant named Sunbird, characterized by its purple flower color, yellow tubular disc florets, relatively large leaves, tall flower stems, and a flower diameter of approximately 35 mm.

1 Drawing Sheet

The present invention comprises a new and distinct cultivar of Aster plant, botanically known as *Aser ericoides,* hereinafter referred to by the cultivar name Sunbird.

The new cultivar was originated from a cross made in a controlled breeding program by the inventor Klara Dehan in Mishmar Hashiva, Israel.

Both the female, or seed, and the male, or pollen parents were cultivars of *Aster ericoides* which are unknown at this time. Both parents are proprietary lines used exclusively for breeding.

Sunbird was discovered and selected by the inventor as a flowering plant within the progeny of the stated cross in a controlled environment in Mishmar Hashiva, Israel. Asexual reproduction of the new cultivar by leaf cuttings performed by the inventor at Mishmar Hashiva, Israel has demonstrated that the combination of characteristics as herein disclosed for the new cultivar are firmly fixed and retained through successive generations of asexual reproduction.

Sunbird has not been observed under all possible environmental conditions. The phenotype may vary somewhat with variations in environment such as temperature, light intensity and daylength, without, however, any variation in genotype. The following observations, measurements and values describe the new cultivar as grown in Mishmar Hashiva, Israel under conditions which closely approximate those generally used in commercial practice.

The following traits have been repeatedly observed and are determined to be basic characteristics of Sunbird which in combination distinguish this Aster as a new and distinct cultivar:

1. Intensive purple flower color.
2. Yellow tubular disc florets.
3. Relatively large leaves.
4. Tall flowering stems, with somewhat larger laterals near bottom becoming shorter near top, producing a conical shape jaundice at the top.
5. Flowers which are approximately 35 mm in diameter when fully open.

The new cultivar can be compared to the aster Sunram. Similar characteristics are ray floret color, foliage color, and good branching. Sunbird is distinguished from Sunram by its slightly larger flower diameter, more flat flower form, shorter plant height, and its wider flower petals.

The accompaning color photographic drawing illustrates a portion of a typical specimen plant of the new cultivar, with partially open and completely open flowers being illustrated. The photo accurately depicts the true ray floret color for Sunbird. The color values noted below are correct.

In the following description, color references are made to The Royal Horticultural Society Colour Chart (R.H.S.), except where general colors of ordinary significance are referred to. Color values were taken in the morning in Mishmar Hashiva, Israel.

Classification:

*Botanical.*—*Aster ericoides* Hybrid cv. Sunbird.

*Commercial.*—Daisy-like spray or garden variety.

Parentage:

*Male parent.*—Unknown seedling of *Aster ericoides.*

*Female parent.*—Unknown seedling of *Aster ericoides.*

Propagation: The new cultivar holds its distinguishing characteristics through successive propagations by leaf cuttings.

INFLORESCENCE

A. Capitulum:

*Form.*—Daisy, round, flat to cup-shaped.

*Type.*—Semi-double, with 1.5 rows of petals.

*Diameter across face.*—Approximately 35 mm.

B. Corolla of ray florets:

*Color (general tonality from a distance of three meters).*—Purple.

*Color (upper surface).*—77B.

*Color (under surface).*—77B.

*Shape.*—Florets are generally narrow and oblong, with apex rounded; slightly concave.

C. Corolla of disc florets:

*Color (mature).*—3A.

*Diameter of disc.*—1 cm.

D. *Flowering period.*—When field grown in natural season, plants planted in June will flower in September. In winter greenhouse production, preferred culture includes approximately four weeks of long-day treatment after pinching until the stems elongate to approximately 10 cm, followed by short days. From the start of short days, flowering occurs in approximately 7 weeks in the fall and 9 weeks in the winter.

E. Reproductive organs:

*Androecium.*—Stamens present on both ray and disc florets and yellow in color; pollen is yellow and found only in the winter season in Israel.

*Gynoecium.*—Present on disc florets; green in color.

PLANT

A. General appearance: Excellent branching and tall, strong stems result in an abundance of flowers; height of main stem is approximately 75 cm.

B. Foliage:

*Color.*—139A.

*Shape.*—Linear, wth occasional downward reflexing at the tip.

*Size.*—typical leaves at upper part of plant (80% from base) are 95 mm in length and 19 mm in width; leaves at bottom of plant (20%) from base) are 100 mm in length and 30 mm in width.

*Margin.*—Entire.

*Arrangement.*—Alternate, with angle acute.

I claim:

1. A new and distinct cultivar of Aster plant named Sunbird, as illustrated and described.

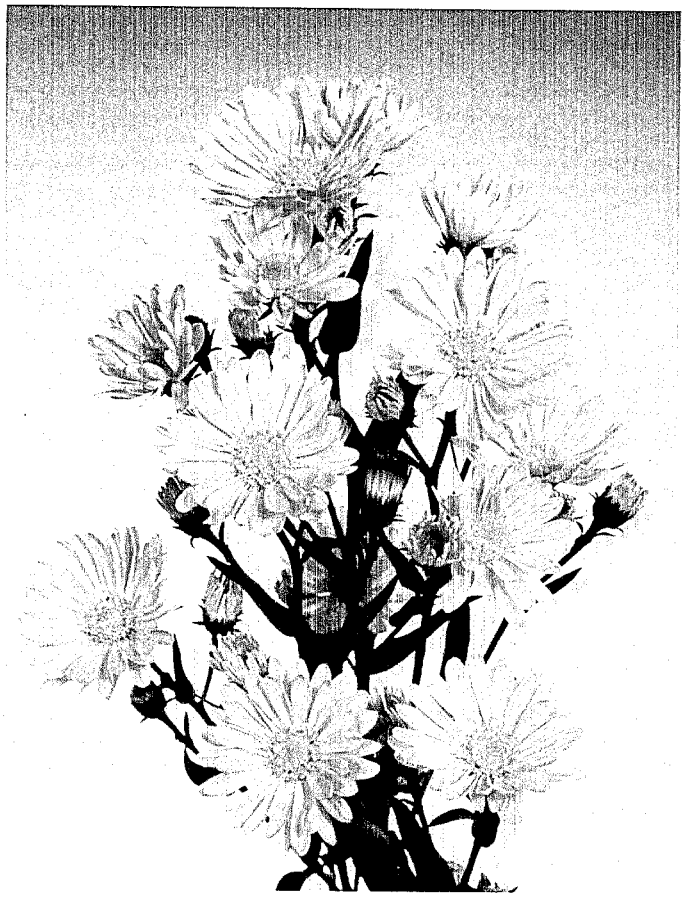

* * * * *